United States Patent [19]

Klumper et al.

[11] Patent Number: 4,555,181
[45] Date of Patent: Nov. 26, 1985

[54] APPARATUS FOR AUTOMATICALLY DETECTING AND EVALUATING THE CHARACTERISTICS OF PRINTS

[75] Inventors: Jan W. Klumper, Alphen a/d Rijn; Huibert Visser, Zevenhuizen, both of Netherlands

[73] Assignee: de Nederlandsche Bank N.V., Amsterdam, Netherlands

[21] Appl. No.: 314,292

[22] Filed: Oct. 23, 1981

[30] Foreign Application Priority Data

Nov. 7, 1980 [NL] Netherlands ............... 8006097

[51] Int. Cl.⁴ .............................................. G07D 7/00
[52] U.S. Cl. ...................................... 356/448; 356/430
[58] Field of Search ............... 356/429, 430, 431, 445, 356/446, 447, 448, 237, 238, 394, 443, 444, 432; 250/571, 572; 355/41; 350/286, 299

[56] References Cited

U.S. PATENT DOCUMENTS

| 2,810,316 | 10/1957 | Snyder | 356/385 |
|---|---|---|---|
| 3,013,467 | 12/1961 | Minsky | 356/432 |
| 3,206,606 | 9/1965 | Burgo et al. | 356/430 |
| 3,453,043 | 7/1969 | Anthony | 350/445 |
| 3,474,254 | 10/1969 | Piepenbrink et al. | 356/430 |
| 3,476,482 | 11/1969 | Howard . | |
| 3,574,469 | 4/1971 | Emerson | 250/571 |
| 3,628,872 | 12/1971 | Miranda | 356/432 |
| 3,675,016 | 7/1972 | Blaisdell . | |
| 3,867,030 | 2/1975 | Tanaka | 355/41 |
| 3,917,414 | 11/1975 | Geis . | |
| 4,004,152 | 1/1977 | Obser et al. | 250/572 |
| 4,197,584 | 4/1980 | Blazek | 356/394 |
| 4,251,157 | 2/1981 | Knor et al. | 250/571 |

FOREIGN PATENT DOCUMENTS

| 0014894 | 9/1980 | European Pat. Off. . |
| 2001049 | 7/1971 | Fed. Rep. of Germany . |
| 2127767 | 10/1972 | France . |
| 2359467 | 2/1978 | France . |
| 2443107 | 6/1980 | France . |
| 7213954 | 4/1973 | Netherlands . |
| 7410463 | 2/1976 | Netherlands . |
| 880135 | 10/1961 | United Kingdom . |
| 1213145 | 11/1970 | United Kingdom . |

Primary Examiner—R. A. Rosenberger
Attorney, Agent, or Firm—Ladas & Parry

[57] ABSTRACT

An apparatus for automatically detecting and evaluating print characteristics comprising an optical detection and comparison means. In particular comparison is made using reflector means which is at the same time a background area for a print in its test position.

7 Claims, 2 Drawing Figures

APPARATUS FOR AUTOMATICALLY DETECTING AND EVALUATING THE CHARACTERISTICS OF PRINTS

The invention relates to an apparatus for automatically detecting and evaluating one or more characteristics of prints by comparison of optically obtained data of a print to be tested with a standard print.

A similar apparatus is known from French patent specification 2 359 467. In this known apparatus a comparison is made on the basis of reflection data of specific portions of a print with standard values for these data which have been recorded in a memory means. A decision about the tested characteristics is taken along the lines of a suitable composed combination value of test data and a correspondingly composed combination value of standard data. Data processing takes place in a computer.

In addition such an apparatus is known from German Auslegeschrift 2 001 049. In this known apparatus the reflection of the surface of a print is detected by simultaneously scanning said print and a reference surface. The reflection of the reference surface is used for calibrating, for each run, a preamplifier which amplifies the electric output signal of the photoelectric transducer responsive to reflected light. In this case a comparison is made of reflection data from specific portions of a print with standard values for these data which are recorded in a memory means.

The comparisons carried out in the known apparatuses by their nature have not been directed to seeking equality but to a classification of data being collected in relation to one or more test limits associated with standard data.

The use of a comparison area when scanning the prints to be tested, as in the apparatus known from German Auslegeschrift 2 001 049, is an inspection mode which eliminates, to a great extent, chance errors resulting from the reflection measurement and in particular such errors resulting from temperature fluctuations and instabilities in the photoelectric detection means. However, the apparatus known from German Auslegeschrift 2 001 049, appears to have insufficient reproducibility in spite of this measure. In addition the measure is time consuming.

SUMMARY OF THE INVENTION

An object of the present invention is an extension of the number of selection grades applied for the evaluation of prints.

A further object of the invention is an optimal use of the light source needed for illuminating the prints to be tested.

Another object of the invention is to improve the signal/noise ratio.

Again a further object of the invention is to introduce in particular novel rejection top limits.

Another object of the invention is to implement an optical calibration of the measurements being carried out without considerably delaying the evaluation process.

According to the invention an apparatus for automatically detecting and evaluating one or more characteristics of prints is characterized by a light source in a first focussing optical system, a reflector means forming the test field background, and a light sensitive detection means in a second focussing optical system, whereby said first focussing optical system and said second focussing optical system are directed to said test field having their optical axes set at equal, but opposite angles with respect to the normal of the test field.

In the apparatus according to the invention print testing is arranged in a reflection configuration so that for example holes in a print (and therefore spacial interruptions in the solid body of the substrate of the print) can be easily detected using a rejection top limit by having the reflector means present.

Further the apparatus according to the invention can incorporate the reflection of the portion of the plane carrying the prints to be tested in between two successive prints enabling a pseudocontinuing standardisation without loss of time. The plane carrying the prints to be tested, then could advantageously be the reflector means.

BRIEF DESCRIPTION OF THE DRAWINGS

The invention with these and further features will be discussed in the following specification of a preferred embodiment, which specification refers to the drawing.

DETAILED DESCRIPTION OF THE PREFERRED EMBODIMENT

Figures 1, 2:
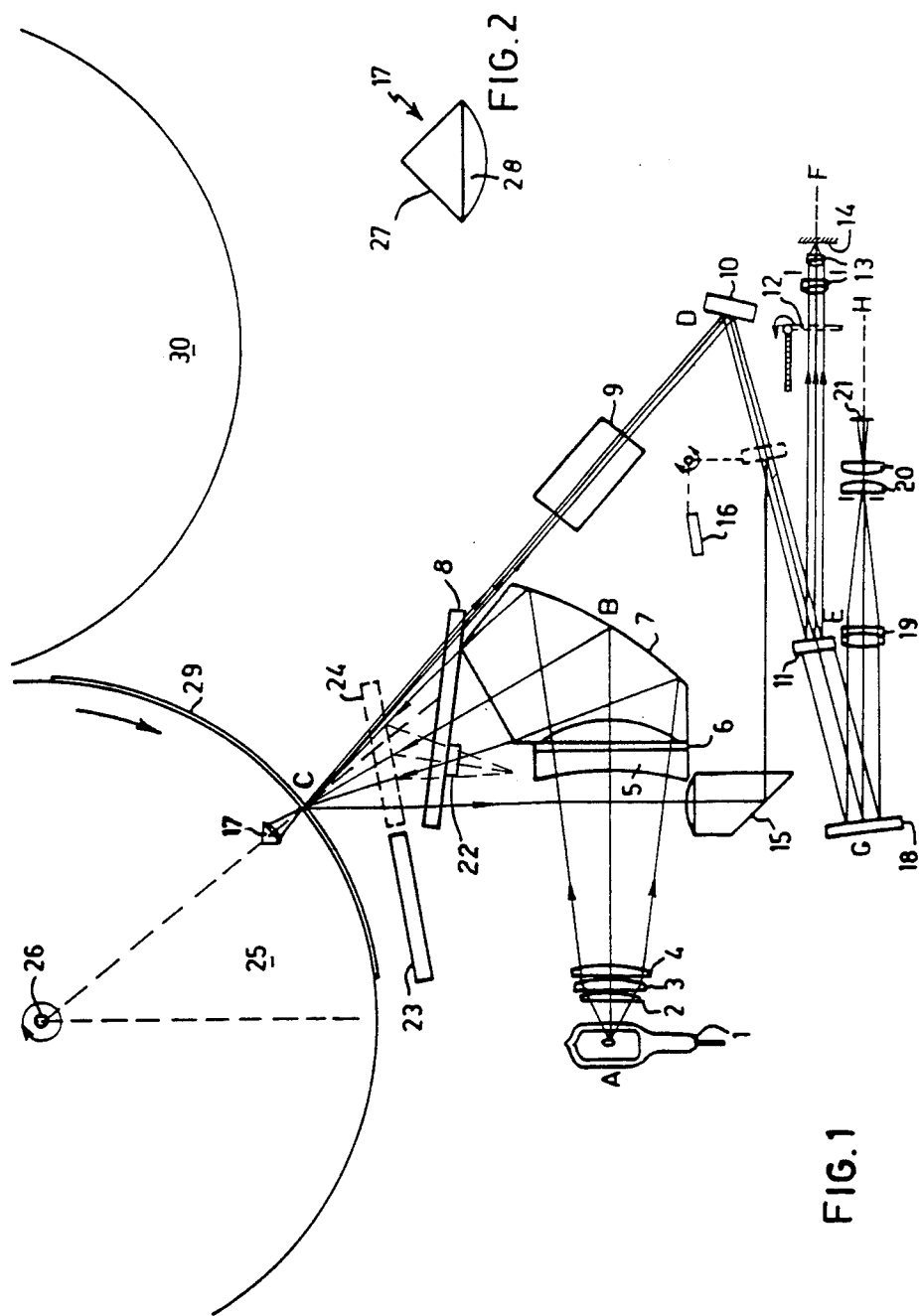
FIG. 1 shows schematically a configuration of the two optical systems in a preferred embodiment of the apparatus according to the invention.
FIG. 2 shows in detail an embodiment of the reflector means according to the invention.

In FIG. 1 a configuration is shown with a first optical system with axes AB and BC and a second optical system with axes CD, DE and EF. The axes BC and CD are set at equal but opposite angles of about 10° with the normal point C on the surface of a drum 25. This drum 25 is part of a conveyor means passing the prints to be tested through the apparatus and in particular across the position defined by point C. The drum 25 is rotating around a shaft 26 in the direction as indicated in the figure. Point C is on a line parallel to shaft 26 of drum 25, said parallel line crossing the drum surface. Scanning of a passing print 29 takes place along said line.

A first optical system comprises a light source 1 having an astigmatic condensor system consisting of lenses 2, 3 and 4, a cylindrical lens 5 joined with a Fresnel lens 6, and finally an optical element 7 operative as a concave mirror. The first optical system images the filament of light source 1 at the surface of drum 25 where position C is located.

The second optical system along the axes CD, DE and EF comprises a lens system 9, mirrors 10 and 11 and an ocular system 13. The second optical system images the narrow illuminated strip at position C on drum 25 onto a photoelectric converter element 14 in a uniform and linear manner. For example the photoelectric converter element 14 may be a so-called solid-state line scanner, type RL 64A of Reticon Corporation. This converter element comprises 64 tightly packed photodiode elements in a single array. The diode-elements of such a converter element are read in sequence. For enabling measurement of the dark current in each of the converter elements a shutter 12 is arranged in the second optical system.

A fixed lens and mirror means 15 and a hinged mirror means 16 permit observations with the converter element 14 of diffuse light reflection in position C.

When mirror 11 is carried out as a dividing mirror (for example as a cold light mirror) a second photoelectric converter means 21 can be put to use along axes EG and GH via a plane mirror 18 and a lens system 19, 20 with a stop slit for detecting a print edge when passing along position C.

The surface of drum 25 may be used as a reflector means to cause saturation of one or more of the diode elements in the photoelectric converter element 14 when the radiation intensity of lamp 1 and the transmission characteristics of the optical systems have been properly adjusted. This adjustment has to be done in such a manner that the presence of a print in position C at least when this print is a sound one, does not cause saturation of any diode element. Holes and dog-ears respectively in the tested print can be easily detected in this manner.

When the adjustment of the lamp, the transmission of the optical systems and the photoelectric converter element have been selected such that the surface reflection value of drum 25 is within the range of measurement of photoelectric converter element 14, this reflection value can be used as a reference for calibrating the complete apparatus in the time between the testing of two prints.

In FIG. 1 a second drum 30 is shown which is part of the conveyor means and feeds prints to drum 25, for example.

When the drum 25 is constructed of disc like parts which present an open space below the supporting face for the prints in the direction of the shaft 26, the reflector means can have a special embodiment, viz. in the form of an optical element 17 as shown in detail in FIG. 2.

Optical element 17 comprises an elongated rectangular prism 27 and a plano convex cylindrical lens 28 being arranged onto the prism 27 opposite the rectangle. Optical element 17 is mounted in such a way that it is directed according to the normal to point C onto the supporting face of drum 25 for prints to be tested, the area as illuminated by the first optical system being located in the focal plane of lens 28. In this construction light being focussed at position C is reflected by reflector means 17 in the direction of axis CD of the second optical system.

The embodiment as shown in FIG. 1 comprises an additional mirror 23 which can reflect the light as focussed by the first optical system, when in position 24 (being shown in dotted lines) to a reference surface 22 which can be a white standard, for example. The same reflect 23 in the position 24 can mirror the reference surface 22 into the second optical system so that the reference surface 22 can enable an absolute calibration of the apparatus.

The reference surface 22 is arranged on the inside of a window pane 8 separating the space comprising the parts of the optical systems from the space in which the conveyor means 25, 30 are located.

It appears that the apparatus as described above distinguished itself by its reproducibility, that is to say, a second test of a lot of prints in the apparatus will produce substantially identical results as a first test. This is the case even without recalibration during the test of the lot. A recalibration in between lots of 10 000 prints for example by means of the white standard 22 and the movable mirror 23 in position 24 appears to be sufficient.

The separation of the optical systems for illumination and detection respectively enables an optimal construction of both systems, each with respect to its aim, which results in a relatively weak light source as far as the illumination is concerned so that heat development is limited as much as possible.

Moveover, the spacial separation between the first optical system and the second optical system results in the heat sensitive parts of the electronic components, such as the photoelectric converter means 14 and 21 experiencing no substantial influence from the development of heat by lamp 1. Although the two optical systems are rather complicated, it appears that both systems are still very stable. It is advantageous that the calibration of the apparatus takes place in substantially the same way as a measurement.

When the optical systems, as is the case here, have been folded, one optical system has an even number of folds (C, D, E, F) and the other system has an odd number of folds (A, B, C) to space apart the light source and the photo-electric converter means as much as possible.

it is noted that the data processing apparatus in which the electric output signals delivered by the photo-electric converter element 14 and possibly by the photoelectric converter means 21, derives its timing control from the run of drum 25 which is therefor detected separately from the test of the prints being transferred on the drum.

We claim:

1. Apparatus for automatically detecting and evaluating one or more characteristics of prints by comparing optically obtained data of a print to be tested with a standard print, comprising a light source in a first focussing optical system, a reflector means located in a region behind and spaced apart from the print to be tested and forming a background for a test field of the print to be tested and a light sensitive detection means in a second focussing optical system, said first focussing optical system and said second focussing optical system being directed to said test field and having their optical axes set at equal. but opposite angles with respect to a normal to the test field said reflection. means being for reflecting light from said first optical system passing through said print, into said second optical system, an area of said test field illuminated by said first focussing optical system being located in a focal plane of said reflection means.

2. Apparatus according to claim 1, further comprising a means for removably positioning a reference area for calibrating purposes in the image plane of said first optical system and in the object plane of said second optical system.

3. Apparatus according to claim 1 or 2, in which the two optical systems are folded, the second optical system having an even number of folds and the first optical system having an odd number of folds.

4. Apparatus according to claim 1 in which the first optical system focuses the light from the light source along a line of said test field and the relector means is configured to reflect light passing through said print back to said test field so that it falls on said line.

5. Apparatus according to claims 1 or 4 in which said reflection means comprises a plano convex cylindrical lens and an elongate rectangular prism arranged on a plane surface of the lens.

6. Apparatus according to claim 5 in which a convex surface of the plano convex lens receives light originating in the first optical system and the plane surface is perpendicular to said normal.

7. Apparatus according to claim 6 in which the first focussing optical system, the second focussing optical system and the reflection means all have a common focus in the test field.

* * * * *